United States Patent
Chen et al.

[11] Patent Number: 5,908,581
[45] Date of Patent: Jun. 1, 1999

[54] RED ORGANIC ELECTROLUMINESCENT MATERIALS

[75] Inventors: Chin H. Chen, Mendon; Kevin P. Klubek, Rochester; Jianmin Shi, Webster, all of N.Y.

[73] Assignee: Eastman Kodak Company, Rochester, N.Y.

[21] Appl. No.: 08/834,574

[22] Filed: Apr. 7, 1997

[51] Int. Cl.$^6$ .......................... C07K 11/06; C07D 455/04
[52] U.S. Cl. .............................. 252/301.16; 252/301.22; 252/301.26; 252/301.32; 428/690; 428/917; 430/48; 546/94; 549/396; 549/398; 549/414; 549/415; 549/426
[58] Field of Search ....................... 546/94; 252/301.22, 252/301.26, 301.32, 301.16; 549/396, 398, 414, 415, 426; 428/690, 917; 430/48

[56] References Cited

U.S. PATENT DOCUMENTS 4,145,215  3/1979  Van Allan .................................. 430/48
4,769,292  9/1988  Tang ....................................... 428/690

*Primary Examiner*—Evelyn Mei Huang
*Attorney, Agent, or Firm*—Raymond L. Owens

[57] ABSTRACT

A red fluorescent material includes a compound of the formula:

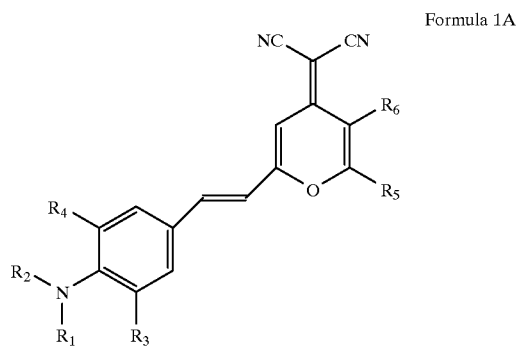

Formula 1A wherein:
  $R_1$, and $R_2$ are individually alkyl of from 1 to 20 carbon atoms, aryl, carbocyclic and other heterocyclic systems; and
  $R_3$, and $R_4$ are individually alkyl of from 1 to 10 carbon atoms, and a branched or unbranched 5 or 6 member substituent ring connecting with $R_1$, $R_2$ respectively; and
  $R_5$ is alkyl of from 2–20 carbon atoms; sterically hindered aryl and heteroaryl; and
  $R_6$ is alkyl of from 1 to 10 carbon atoms, and a 5 or 6-member carbocyclic ring connecting with $R_5$.

10 Claims, 4 Drawing Sheets

RED ORGANIC ELECTROLUMINESCENT MATERIALS

CROSS REFERENCE TO RELATED APPLICATION

Reference is made to commonly-assigned U.S. patent application Ser. No. 08,834,577 filed Apr. 7, 1997, entitled "Red Organic Electroluminescent Devices" by Chen et al, the teaching of which is incorporated herein.

FIELD OF THE INVENTION

This invention relates to novel red fluorescent materials that can be used as dopants in devices.

BACKGROUND OF THE INVENTION

One application for using red fluorescent materials is in organic EL (electroluminescent) devices. Organic EL devices are known to be highly efficient and are capable of producing a wide range of colors. Useful applications such as flat-panel displays have been contemplated. Representative of earlier organic EL devices are Gurnee et al U.S. Pat. No. 3,172,862, issued Mar. 9, 1965; Gurnee U.S. Pat. No. 3,173,050, issued Mar. 9, 1965; Dresner, "Double Injection Electroluminescence in Anthracene," RCA Review, Vol. 30, pp. 322–334, 1969; and Dresner U.S. Pat. No. 3,710,167, issued Jan. 9, 1973. Typical organic emitting materials were formed of a conjugated organic host material and a conjugated organic activating agent having condensed benzene rings. Naphthalene, anthracene, phenanthrene, pyrene, benzopyrene, chrysene, picene, carbazole, fluorene, biphenyl, terphenyls, quarterphenyls, triphenylene oxide, dihalobiphenyl, trans-stilbene, and 1,4-diphenylbutadiene were offered as examples of organic host materials. Anthracene, tetracene, and pentacene were named as examples of activating agents. The organic emitting material was present as a single layer medium having a thickness much above 1 micrometer. Thus, this organic EL medium was highly resistive and the EL device required a relatively high voltage (>100 volts) to operate.

The most recent discoveries in the art of organic EL device construction have resulted in devices having the organic EL medium consisting of extremely thin layers (<1.0 micrometer in combined thickness) separating the anode and cathode. Herein, the organic EL medium is defined as the organic composition between the anode and cathode electrodes. In a basic two-layer EL device structure, one organic layer is specifically chosen to inject and transport holes and the other organic layer is specifically chosen to inject and transport electrons. The interface between the two layers provides an efficient site for the recombination of the injected hole-electron pair and resultant electroluminescence. The extremely thin organic EL medium offers reduced resistance, permitting higher current densities for a given level of electrical bias voltage. Since light emission is directly related to current density through the organic EL medium, the thin layers coupled with increased charge injection and transport efficiencies have allowed acceptable light emission levels (e.g. brightness levels capable of being visually detected in ambient light) to be achieved with low applied voltages in ranges compatible with integrated circuit drivers, such as field effect transistors.

Further improvement in organic EL devices such as color, stability, efficiency and fabrication methods have been disclosed in U.S. Pat. Nos.: 4,356,429; 4,539,507; 4,720,432; 4,885,211; 5,151,629; 5,150,006; 5,141,671; 5,073,446; 5,061,569; 5,059,862; 5,059,861; 5,047,687; 4,950,950; 4,769,292, 5,104,740; 5,227,252; 5,256,945; 5,069,975, and 5,122,711; 5,366,811; 5,126,214; 5,142,343; 5,389,444; 5,458,977.

For the production of full-color EL display panel, it is necessary to have efficient red, green and blue (RGB) EL materials with proper chromaticity and sufficient luminance efficiency. The guest-host doped system offers a ready avenue for achieving such an objective, mainly because a single host with optimized transport and luminescent properties may be used together with various guest dopants leading to EL of desirable hue.

A doped EL system based on the principle of guest-host energy transfer to effect the spectral shift from tris-(8-hydroxyquinolinato)aluminum (Alq) to the dopant molecules has been disclosed by Tang et al [U.S. Pat. No. 4,769,292]. Alq is a suitable host for red EL emitters since its emission at 530 nm is adequate to sensitize guest EL emission in the red spectral region. The preferred dopants chosen to provide the red emission in this prior art were 4-(dicyanomethylene)-2-methyl-6-(p-dimethylaminostyryl)-4H-pyran (DCM) and the julolidyl derivative DCJ (Structure 1, [supra] R=H). These molecules generally have a high photoluminescence (PL) quantum yield (>70% in dilute solution) and the position of the emission maxima can be readily shifted by certain modification of the DCM structure. Furthermore, in both PL and EL, a significant red-shift in emissions was observed with increasing dopant concentration in the Alq host. Thus, efficient red EL emitters with suitable hue can be found among molecules in this DCM class.

Other considerations in the fields of fluorescence and electroluminescence applications are the purity of fluorescent materials and the degree of synthetic complexities, including consideration of yield loss due to post-process purification procedures. In the aforementioned patent, the preparation and subsequent purification of both DCM and DCJ are complicated by the inevitable generation of significant amount of an unwanted corresponding bis-condensed dye caused by the further reaction of the "active" methyl group present in the fluorescent dye molecules. The bis-condensed byproduct of DCM has been identified as 4-(dicyanomethylene)-2,6-bis(p-dimethylaminostyryl)-4H-pyran which absorbs the DCM fluorescence band, thus diminishes or extinguishes its fluorescence (Hammond, *Optics Comm.*, 1989, 29, 331). Furthermore, once the bis-condensed dye is formed in the reaction mixture, it is difficult to remove, particularly in a large scale preparation. Accordingly, it is desirable to provide a fluorescent compound useful in EL applications which has a relatively high EL efficiency, a desired emission in the red region of the spectrum and is easy to synthesize and to purify.

Chen et. al. in a publication titled, "Design and Synthesis of Red Dopants for Electroluminescence" (*Proc. $2_{nd}$ Internat. Sym. Chem. Functional Dyes*, 1992, 536) describes the synthesis and EL properties of DCJT (Structure 1, R=CH$_3$) by introducing steric spacer groups which reduce undesirable concentration quenching, thus providing enhanced EL efficiency in the desired red spectral region. However, the preparation and subsequent purification of DCJT are also complicated by the inevitable generation of significant amount of an unwanted bis-condensed dye (Structure 2 [supra], R=CH$_3$), which only has a very weak fluorescence in the near infra-red region of the visible spectrum. The contamination of this unwanted byproduct tends to decrease the fluorescence efficiency of DCJT, counteracting the effect of reduction of concentration quenching. When the above mentioned fluorescent compounds are used as dopants in the EL host matrices, such as for example, Alq, the aforementioned undesirable concentration quenching result in correspondingly reduced EL efficiency.

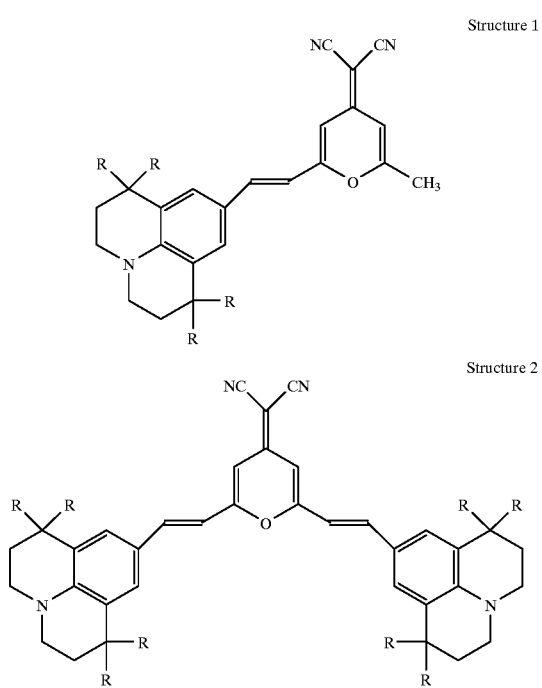

Structure 1

Structure 2

Another application for red fluorescent materials is as a laser dye in a dye laser which produces red light Numerous organic compounds in the DCM class are known to be useful in dye lasers. However, they suffer from a number of disadvantages in that the dye materials are frequently difficult to synthesize and purify. One of the ways to circumvent the difficulties in synthesis and subsequent purification to remove the unwanted bis-condensed byproduct is to substitute the methyl group in Structure 1 with a phenyl group. For example, the intermediate 4-(dicyanomethylene)-2-methyl-6-phenyl-4H-pyran and dyes derived thereof has been disclosed in U.S. Pat. No. 4,145,215. However, due to the mobility of the phenyl group which tends to enhance the probability for nonradiative decay (K. H. Drexhage, *Dye Lasers* Topics in Applied Physics, ed., F. P. Schafer, Springer, Berlin, Vol. 1, 1973, p.144), dyes synthesized from this unsymmetrical 4-(dicyanomethylene)-2-methyl-6-phenyl-4H-pyran are not very fluorescent and thus, are not considered as good candidates for DCM replacement. Furthermore, due to the conjugation of the phenyl group with the dye DCM-chromophore, the phenyl substituted DCM type of fluorescent dyes are considerably broadened and shifted too deep to the red. As a result, the dyes derived from 4-(dicyanomethylene)-2-methyl-6-phenyl-4H-pyran do not retain the similar spectral properties of the corresponding DCM dyes.

SUMMARY OF THE INVENTION

It is an object of the present invention to provide an improved red fluorescent material which does not contain the "active methyl" group as that depicted in Structure 1.

It is another object of the present invention to provide an improved red fluorescent material which has high luminescence efficiency.

It is another object of the present invention to provide an improved red fluorescent material which fluoresces in the red region of the visible spectrum.

This object is achieved by a red fluorescent material comprising a compound of the formula:

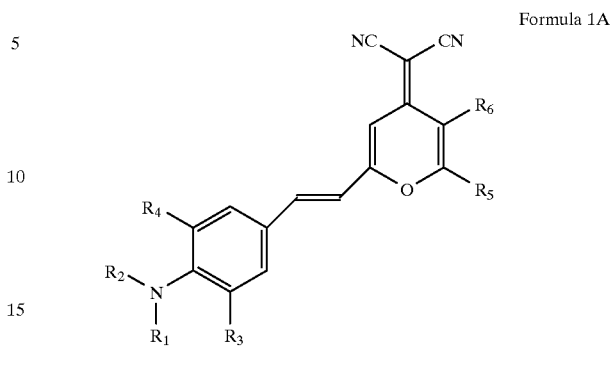

Formula 1A wherein:
  $R_1$, and $R_2$ are individually alkyl of from 1 to 20 carbon atoms, aryl, carbocyclic and other heterocyclic systems; and
  $R_3$, and $R_4$ are individually alkyl of from 1 to 10 carbon atoms, and a branched or unbranched 5 or 6 member substituent ring connecting with $R_1$, $R_2$ respectively; and
  $R_5$ is alkyl of from 2–20 carbon atoms; sterically hindered aryl and heteroaryl; and
  $R_6$ is alkyl of from 1 to 10 carbon atoms, and a 5 or 6-member carbocyclic ring connecting with $R_5$.

It is a feature of the present invention that when the compound is applied to EL devices it provides a fluorescent compound devoid of chemical reactivity of the extra "active" methyl group, thereby avoiding the formation of the unwanted bis-condensed dye in the reaction product mixture. Moreover, the fluorescent compound has EL performance and chromaticity characteristics comparable to those of DCJT.

When used as a dye material in other devices such as dye lasers and luminescent solar concentrators, fluorescent inks and other applications, the material is particularly useful.

BRIEF DESCRIPTION OF THE DRAWINGS

These and other advantages of this invention can be better appreciated by reference to the following detailed description considered in conjunction with the drawings in which.

DETAILED DESCRIPTION OF THE PREFERRED EMBODIMENTS

Figure 1:
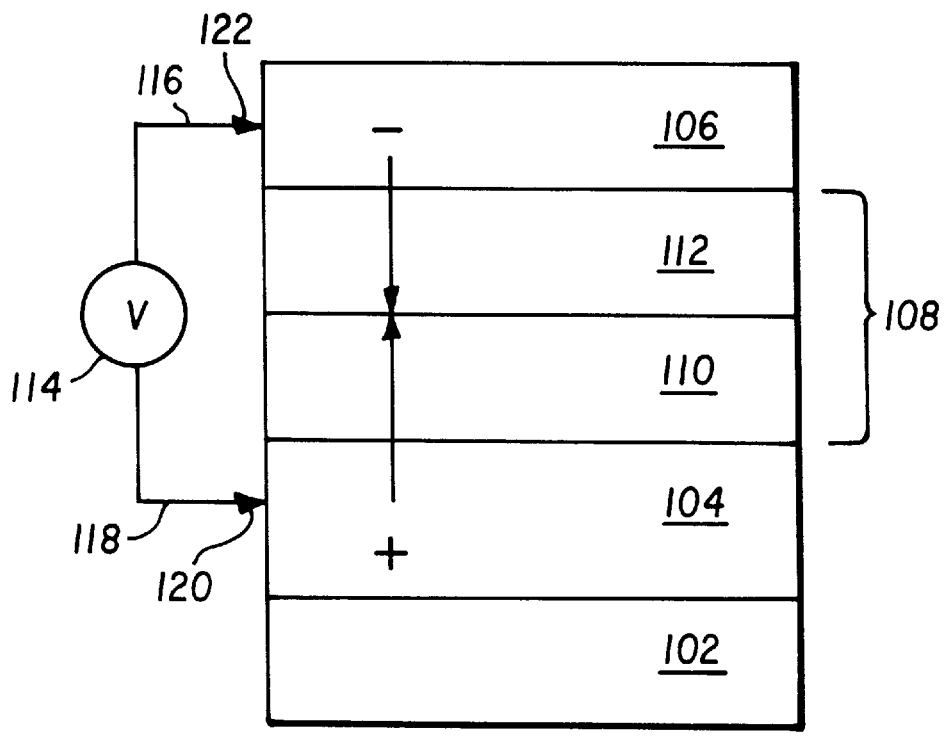
FIGS. 1, 2, and 3 are schematic diagrams of the multilayer structures of preferred EL devices which can employ the compound of this invention.

One particularly useful application of the compound is in EL devices. An EL device 100 which uses a compound according to the invention is schematically illustrated in FIG. 1. The support is layer 102 which is an electrically insulating and optically transparent material such as glass or plastic. Anode 104 is separated from cathode 106 by an organic EL medium 108, which, as shown, consists of two superimposed layers of organic thin films. Layer 110 located on the anode forms a hole-transport layer of the organic EL medium. Located above the hole-transport layer is layer 112, which forms an electron-transport layer of the organic EL medium. The anode and the cathode are connected to an external AC or DC power source 114 by conductors 116 and 118, respectively. The power source can be pulsed, periodic, or continuous.

In operation, the EL device can be viewed as a diode which is forward biased when the anode is at a higher potential then the cathode. Under these conditions, holes (positive charge carriers) are injected from the anode into the hole-transport layer, and electrons are injected into the electron-transport layer. The injected holes and electrons each migrate toward the oppositely charged electrode, as shown by the arrows 120 and 122, respectively. This results in hole-electron recombination and a release of energy in part as light, thus producing electroluminescence.

The region where the hole and electron recombine is known as the recombination zone. The two-layer device structure is designed specifically to confine the recombination at the vicinity near the interface between the hole-transport and the electron-transport layer where the probability for producing electroluminescence is the highest. This recombination confinement scheme has been disclosed by Tang and Van Slyke [Applied Physics Letters, Volume 51, Page 913, 1987] and is done by choosing carrier injecting electrodes of suitable work-functions and transport materials of a proper carrier mobility. Away from this interface between the organic layers and in particular at or near the injecting electrodes, the recombination of hole and electron would generally be much less radiative due to the effect of radiative quenching by a conducting surface.

Figure 2:
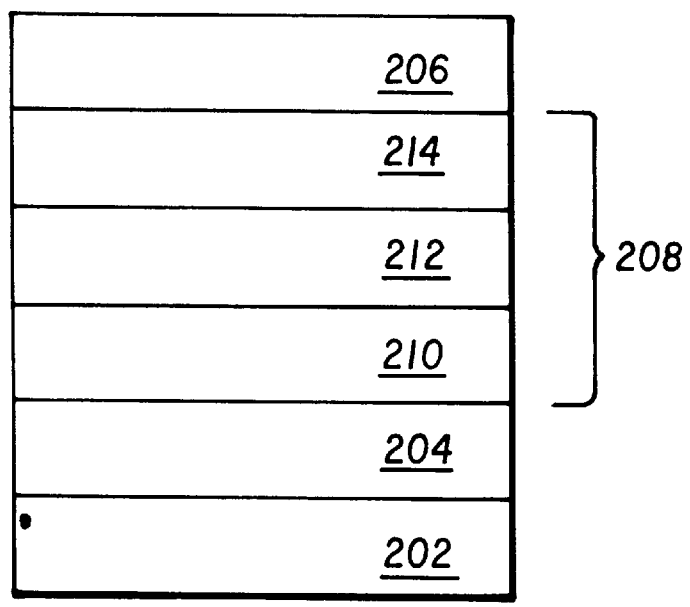

Organic EL device 200 shown in FIG. 2 is illustrative of another EL device which can use the compound of the present invention. The insulating and transparent support is layer 202. The anode 204 is separated from the cathode 206 by an EL medium 208, which, as shown, consists of three superimposed layers of organic thin films. Layer 210 adjacent to anode 204 is the hole-transport layer. Layer 214 adjacent to cathode 206 is the electron-transport layer. Layer 212 which is in between the hole-transport layer and the electron transport layer is the luminescent layer. This luminescent layer also serves as the recombination layer where the hole and electron recombines.

The configurations of devices 100 and 200 are similar, except that an additional luminescent layer is introduced in device 200 to function primarily as the site for hole-electron recombination and thus electroluminescence. In this respect, the functions of the individual organic layers are distinct and can therefore be optimized independently. Thus, the luminescent or recombination layer can be chosen to have a desirable EL color as well as a high luminance efficiency. Likewise, the electron and hole transport layers can be optimized primarily for the carrier transport property.

Figure 3:
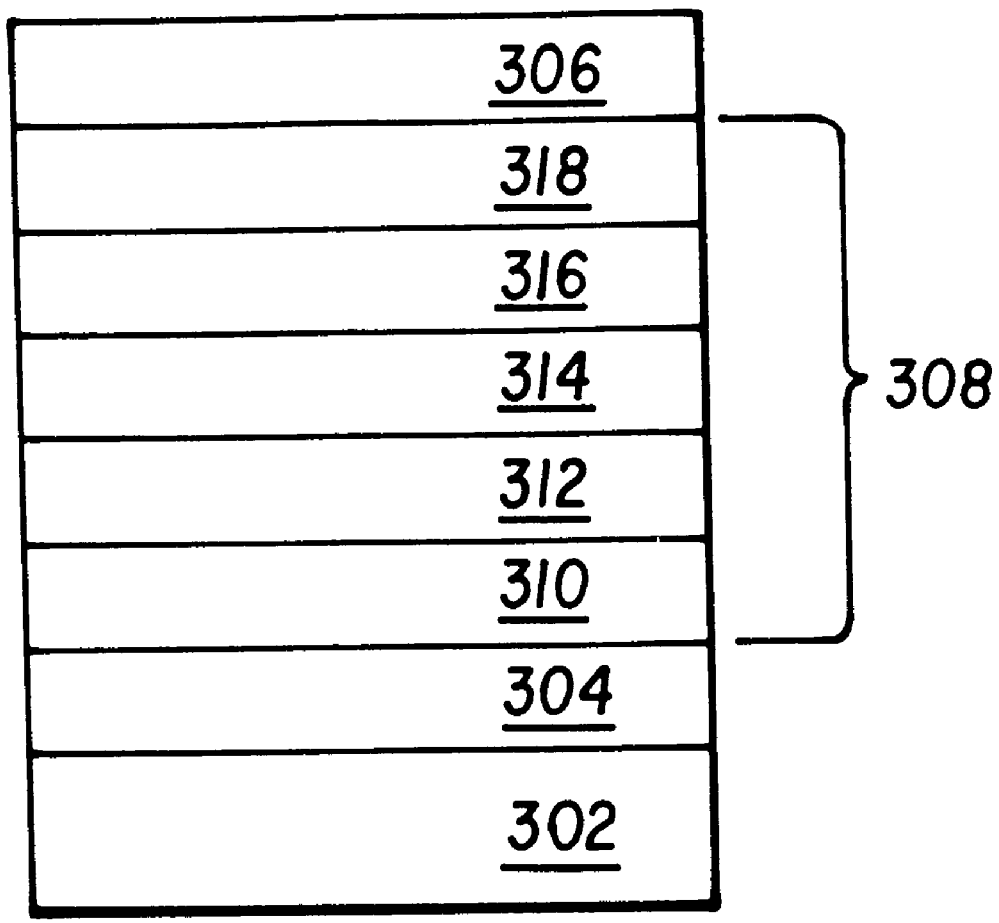

Organic device 300 shown in FIG. 3 is illustrative of yet another EL device which can use the compound of the present invention. The insulating and transparent support is layer 302. The anode 304 is separated from the cathode 306 by an EL medium 308, which, as shown, consists of five superimposed layers of organic thin films. Located on top of the anode layer 304 are, in sequence, the hole-injection layer 310, the hole-transport layer 312, the luminescent layer 314, the electron-transport layer 316, and the electron-injection layer 318. The structure of device 300 is similar to device 200, except that a hole-injection layer and an electron injection layers are added to improve the injection efficiency of the respective anode and cathode. It is understood that an EL device may be constructed having either the hole or electron injection layer present in the organic EL medium without unduly compromising the device performance.

One particular compound that is effective is

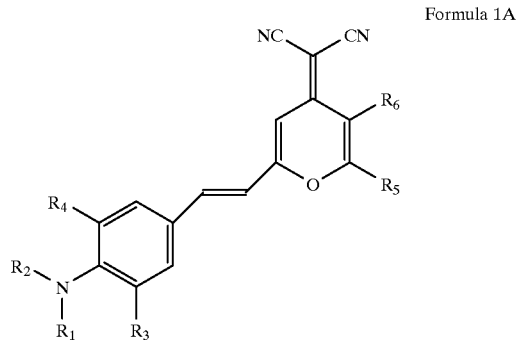

Formula 1A wherein:

$R_1$, and $R_2$ are individually alkyl of from 1 to 20 carbon atoms, aryl, carbocyclic and other heterocyclic systems; and $R_3$, and $R_4$ are individually alkyl of from 1 to 10 carbon atoms, and a branched or unbranched 5 or 6 member substituent ring connecting with $R_1$, $R_2$ respectively; and $R_5$ is alkyl of from 2–20 carbon atoms; sterically hindered aryl and heteroaryl; perhaloalkyl of 1–10 carbon atoms and $R_6$ is alkyl of from 1 to 10 carbon atoms, and a 5 or 6-member carbocyclic ring connecting with $R_5$.

The term "sterically hindered" means a function moiety that restricts free rotation about a C—C single bond.

In the above compound $R_1$ and $R_2$ can be methyl, ethyl, propyl, n-butyl, aryl or heteroaryl, including phenyl and, furyl, thienyl, pyridyl, and other heterocyclic systems, $R_3$ and $R_4$ are methyl, ethyl, propyl, n-butyl, i-propyl, t-butyl, sec-butyl, t-amyl, wherein $R_3$ and $R_4$ are arranged respectively with $R_1$ and $R_2$ as follows $R_1$, $R_3$ =$R_2$, $R_4$ =[$CH_2CH_2$], [$CH_2CH_2CH_2$], [$CH_2CH_2C(CH_3)_2$] and $R_5$ is ethyl, propyl, n-butyl, i-propyl, t-butyl, sec-butyl, t-amyl, neopentyl and the like; sterically hindered aryl, for example, 1-naphthyl, 9-anthracenyl, pyrenyl, perylenyl, ortho-substituted aryl of from 1–10 carbon atoms, including mesityl, 2,4-dimethylphenyl, 2-methylphenyl and the like; perhaloalkyl of from 1–10 carbon atoms, including trifluoromethyl, pentafluoroethyl, perfluoroalkyl and wherein when the carbocylic ring is connected with $R_5$ it forms the following structure $R_5$, $R_6$=(—$CH_2CH_2CH_2$—) and (—$CH_2CH_2CH_2CH_2$—).

In EL devices the following compound structure has been found to be particularly effective.

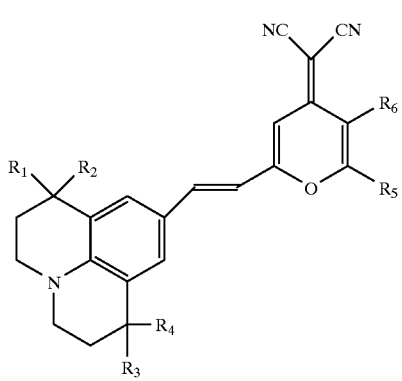

Formula 1B wherein:

R₁, R₂, R₃, and R₄ are individually alkyl of from 1 to 10 carbon atoms; halogen;

R₅ is alkyl of from 2–20 carbon atoms; sterically hindered aryl and heteroaryl; and R₆ is alkyl of from 1 to 10 carbon atoms, and a 5 or 6-member carbocyclic ring connecting with R₅.

In the above compound R₁, R₂, R₃ and R₄ can be methyl, ethyl, propyl, n-butyl, i-propyl; aryl or heteroaryl, or including, phenyl and, furyl, thienyl, pyridyl, and other heterocyclic systems; or halogen substituents such as chloro, fluoro and wherein R₅ is ethyl, propyl, n-butyl, i-propyl, t-butyl, sec-butyl, t-amyl, neopentyl and the like; sterically hindered aryl, for example, 1-naphthyl, 9-anthracenyl, pyrenyl, perylenyl, ortho-substituted aryl of from 1–10 carbon atoms, including mesityl, 2,4-dimethylphenyl, 2-methylphenyl and the like; perhaloalkyl of from 1–10 carbon atoms, including trifluoromethyl, pentafluoroethyl, perfluoroalkyl and wherein when the carbocylic ring is connected with R₅ it forms the following structure R₅, R₆=(—CH₂CH₂CH₂—) and (—CH₂CH₂CH₂CH₂—).

The substrate for the EL devices 100, 200, and 300 is electrically insulating and light transparent. The light transparent property is desirable for viewing the EL emission through the substrate. For applications where the EL emission is viewed through the top electrode, the transmissive characteristic of the support is immaterial, and therefore any appropriate substrate such as opaque semiconductor and ceramic wafers can be used. Of course, it is necessary to provide in these device configurations a light transparent top electrode.

The composition of the organic EL medium is described as follows, with particular reference to device structure 300.

A layer containing a porphyrinic compound forms the hole injecting layer of the organic EL device. A porphyrinic compound is any compound, natural or synthetic, which is derived from or includes a porphyrin structure, including porphine itself. Any of the prophyrinic compounds disclosed by Adler, U.S. Pat. No. 3,935,031 or Tang U.S. Pat. No. 4,356,429, the disclosures of which are here incorporated by reference, can be employed.

Preferred porphyrinic compounds are those of structural formula (II):

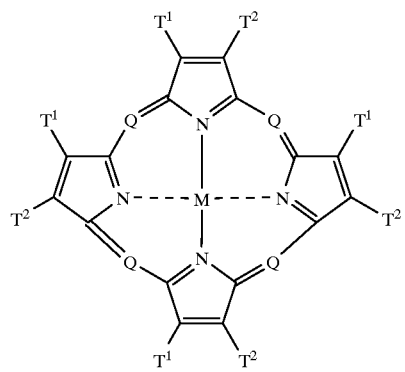

(II)

wherein

Q is —N= or —C(R)=;

M is a metal, metal oxide, or metal halide;

R is hydrogen, alkyl, aralkyl, aryl, or alkaryl; and

T¹ and T² represent hydrogen or together complete a unsaturated six member ring, which can include substituents, such as alkyl or halogen. Preferred six membered rings are those formed of carbon, sulfur, and nitrogen ring atoms. Preferred alkyl moieties contain from about 1 to 6 carbon atoms while phenyl constitutes a preferred aryl moiety.

In an alternative preferred form the porphyrinic compounds differ from those of structural formula (I) by substitution of two hydrogens for the metal atom, as indicated by formula (III):

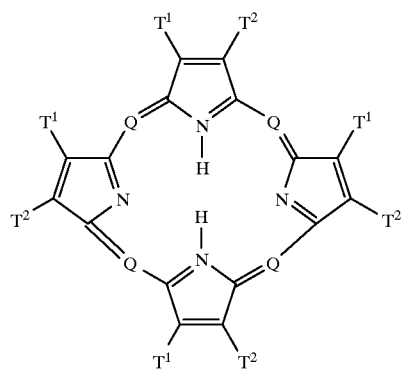

(III)

Highly preferred examples of useful porphyrinic compounds are metal free phthalocyanines and metal containing phthalocyanines. While the porphyrinic compounds in general and the phthalocyanines in particular can contain any meal, the metal preferably has a positive valence of two or higher. Exemplary preferred metals are cobalt, magnesium, zinc, palladium, nickel, and, particularly, copper, lead, and platinum.

Illustrative of useful porphyrinic compounds are the following:

Prophine 1,10,15,20-tetraphenyl-21H,23H-porphine copper (II)

1,10,15,20-tetrapheyl-21H,23H-porphine zinc (II)

Copper phthlocyanine

Chromium phthalocyanine fluoride

The hole transporting layer of the organic EL device contains at least one hole transporting aromatic tertiary amine, where the latter is understood to be a compound containing at least one trivalent nitrogen atom that is bonded only to carbon atoms, at least one of which is a member of an aromatic ring. In one form the aromatic tertiary amine can be an arylamine, such as a monarylamine, diarylamine, triarylamine, or a polymeric arylamine. Exemplary monomeric triarylamines are illustrated by Klupfel et al U.S. Pat. No. 3,180,730. Other suitable triarylamines substituted with vinyl or vinyl radicals and/or containing at least one active hydrogen containing group are disclosed by Brantley et al U.S. Pat. Nos. 3,567,450 and 3,658,520.

Another class of aromatic tertiary amines are those which include at least two aromatic tertiary amine moieties. Such compounds include those represented by structural formula (IV).

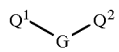

(IV)

wherein
$Q^1$ and $Q^2$ are independently aromatic tertiary amine moieties and
G is a linking group such as an arylene, cycloalkylene, or alkylene group of a carbon to carbon bond.

A preferred class of triarylamines satisfying structural formula (IV) and containing two triarylamine moieties are those satisfying structural formula (V):

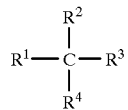

(V)

where
$R^1$ and $R^2$ each independently represents a hydrogen atom, an aryl group, or an alkyl group or $R^1$ and $R^2$ together represent the atoms completing a cycloalkyl group and
$R^3$ and $R^4$ each independently represents an aryl group which is in turn substituted with a diaryl substituted amino group, as indicated by structural formula (VI):

(VI)

wherein $R^5 R^6$ are independently selected aryl groups.

Another preferred class of aromatic tertiary amines are tetraaryldiamines. Preferred tetraaryldiamines include two diarylamino groups, such as indicated by formula (VII), linked through an arylene group:

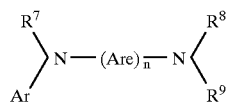

wherein
Are is an arylene group,
n is an integer of from 1 to 4, and

Ar, $R^7$, $R^8$, and $R^9$ are independently selected aryl groups.

The various alkyl, alkylene, aryl, and arylene moieties of the foregoing structural formulae (IV), (V), (VII), can each in turn be substituted. Typical substituents including alkyl groups, alkoxy groups, aryl groups, aryloxy groups, and halogen such as fluoride, chloride, and bromide. The various alkyl and alkylene moieties typically contain from about 1 to 6 carbon atoms. The cycloalkyl moieties can contain from 3 to about 10 carbon atoms, but typically contain five, six, or seven ring carbon atoms—e.g., cyclopentyl, cyclohexyl, and cycloheptyl ring structures. The aryl and arylene moieties are preferably phenyl and phenylene moieties.

Illustrative of useful hole transport compounds are the following:

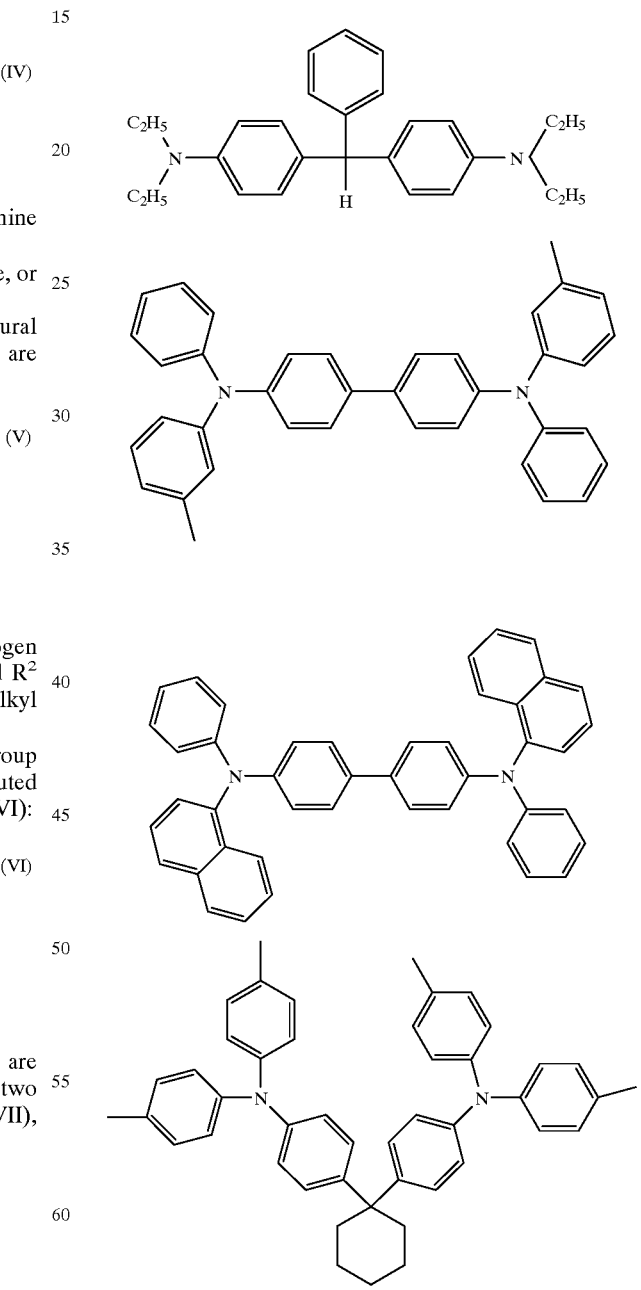

The luminescent layer of the organic EL medium comprises of a luminescent or fluorescent material where electroluminescence is produced as a result of electron-hole pair recombination in this region. In the simplest construction, the luminescent layer comprises of a single component, that is a pure material with a high fluorescent efficiency. A well known material is tris (8-quinolinato) Aluminum, (Alq), which produces excellent green electroluminescence. A preferred embodiment of the luminescent layer comprises a multi-component material consisting of a host material doped with one or more components of fluorescent dyes. Using this method, highly efficient EL devices can be constructed. Simultaneously, the color of the EL devices can be tuned by using fluorescent dyes of different emission wavelengths in a common host material. This dopant scheme has been described in considerable details for EL devices using Alq as the host material by Tang et [J. Applied Physics, Vol. 65, Pages 3610–3616, 1989; U.S. Pat. No. 4,769,292].

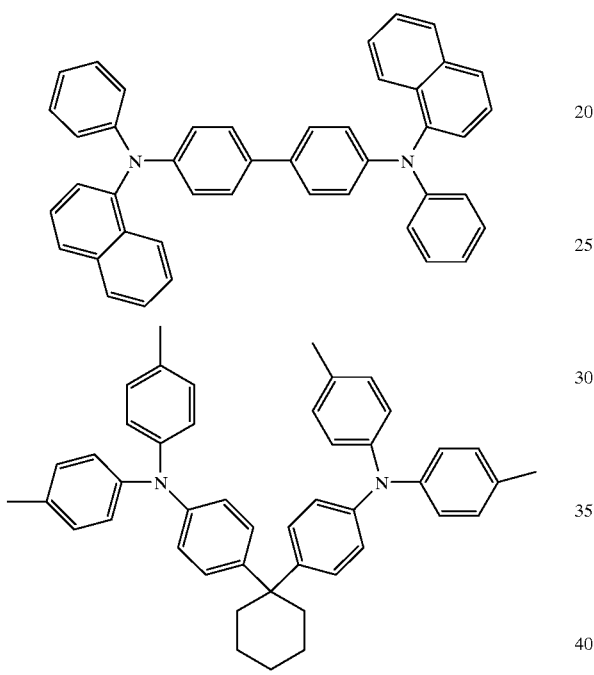

The luminescent layer of the organic EL medium comprises of a luminescent or fluorescent material where electroluminescence is produced as a result of electron-hole pair recombination in this region. In the simplest construction, the luminescent layer comprises of a single component, that is a pure material with a high fluorescent efficiency. A well known material is tris (8-quinolinato) Aluminum, (Alq), which produces excellent green electroluminescence. A preferred embodiment of the luminescent layer comprises a multi-component material consisting of a host material doped with one or more components of fluorescent dyes. Using this method, highly efficient EL devices can be constructed. Simultaneously, the color of the EL devices can be tuned by using fluorescent dyes of different emission wavelengths in a common host material. This dopant scheme has been described in considerable details for EL devices using Alq as the host material by Tang et [J. Applied Physics, Vol. 65, Pages 3610–3616, 1989; U.S. Pat. No. 4,769,292].

An important relationship for choosing a fluorescent dye as a dopant capable of modifying the hue of light emission when present in a host material is a comparison of their bandgap potential which is defined as the energy difference between the highest occupied molecular orbital and the lowest unoccupied molecular orbital of the molecule. For efficient energy transfer from the host to the dopant molecule, a necessary condition is that the bandgap of the dopant is smaller than that of the host material. An advantage of using a green host such as Alq is that its bandgap is sufficiently large to effect energy transfer to fluorescent dyes emitting in the red, such as DCJT and improved red fluorescent compounds described in this invention.

In the practice of the present invention, the host material forming the EL luminescent layer where light is emitted in response to electron-hole recombination comprises of Alq. The dopants for the host Alq include the red fluorescent dyes as depicted in Formula IA and IB above. Efficient red electroluminescence can be readily obtained when this red dopant is used in layer 112 of FIG. 1, layer 212 of FIG. 2 or layer 314 of FIG. 3.

The following molecular structures constitute specific examples of preferred red fluorescent dopants satisfying the requirement of the invention:

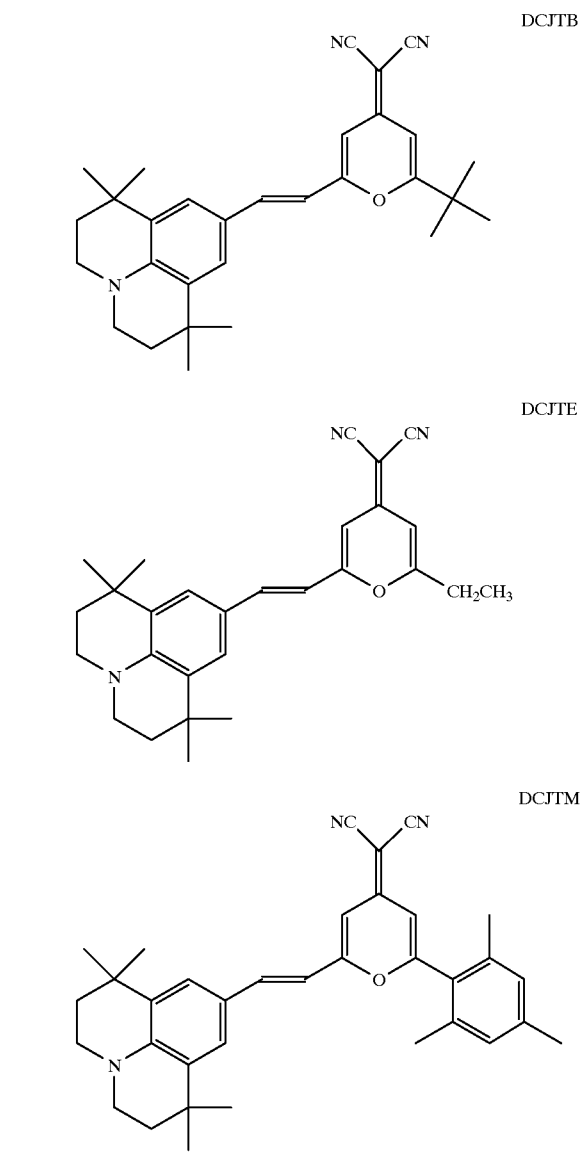

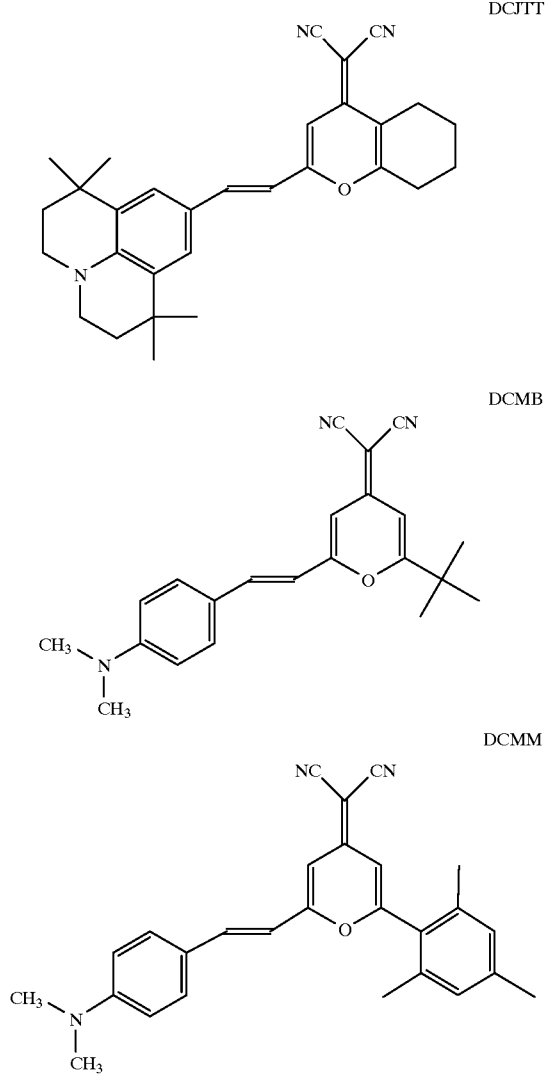

DCJTT

DCMB

DCMM

Scheme 1 shows the synthetic sequence for the new fluorescent dyes disclosed in this invention. Comparison of fluorescence properties of these new materials with DCM and DCJT is made in Table 1.

TABLE 1

Comparison of Fluorescent Properties Of DCM, DCJT and the New Fluorescent Dyes

| Dyes | Radiance[a] | Luminance[a] | λ max[b] |
|------|-------------|--------------|----------|
| DCM   | 1.0  | 1.0  | 585 nm |
| DCMB  | 1.36 | 1.44 | 583 nm |
| DCMM  | 1.53 | 1.43 | 597 nm |
| DCJT  | 1.58 | 0.89 | 618 nm |
| DCJTB | 1.70 | 1.01 | 615 nm |
| DCJTE | 1.52 | 0.88 | 622 nm |
| DCJTT | 0.97 | 0.51 | 619 nm |
| DCJTM | 1.46 | 0.67 | 636 nm |

[a]Relative to DCM
[b]Measured in 1,2-dichloroethane

Figure 4:
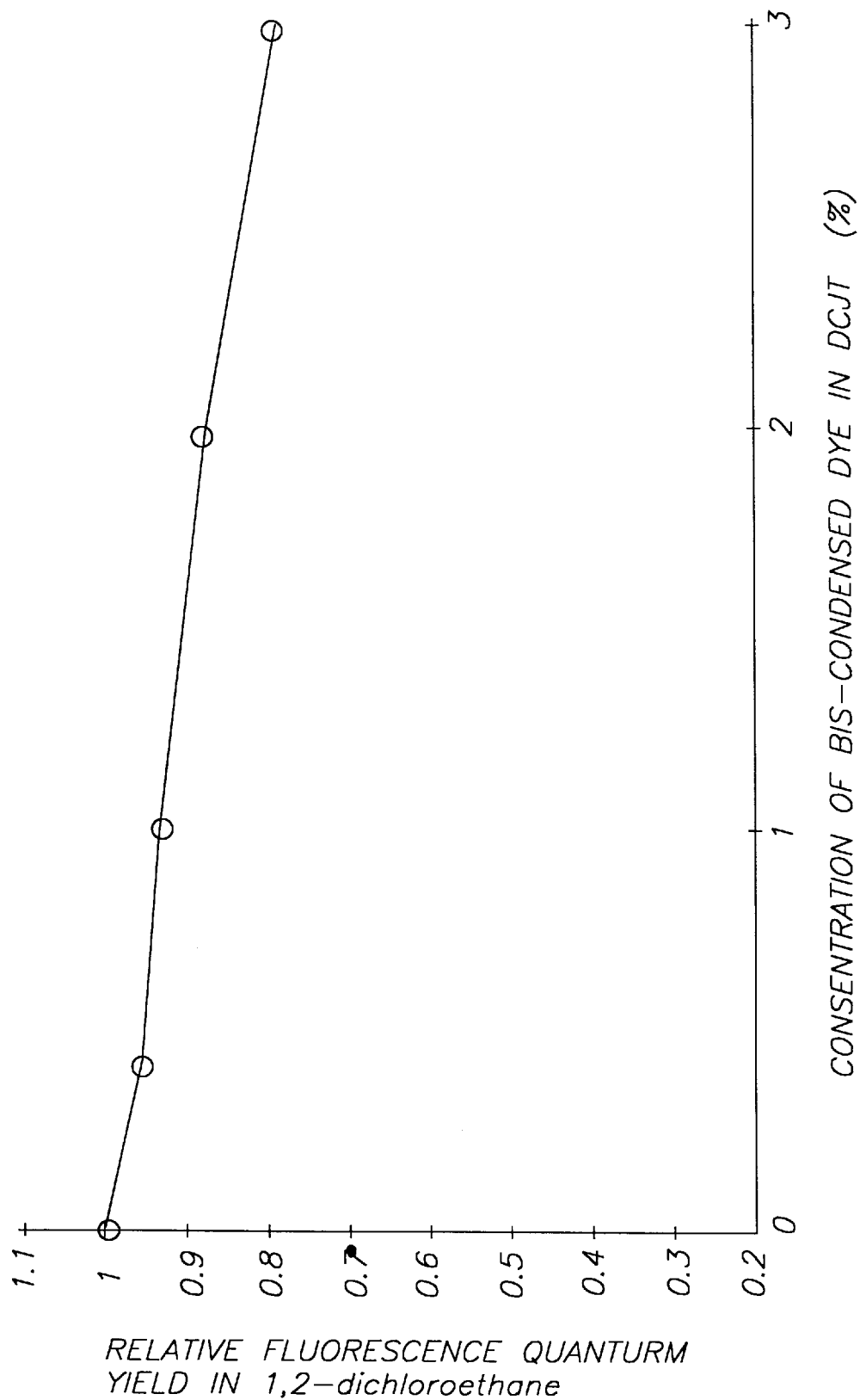
FIG. 4 shows the effect of bis-condensed byproduct of DCJT (Structure 2, R=CH$_3$) concentration on the fluorescence quantum efficiency of DCJT.

The bis-condensed byproduct of DCJT synthesis (Structure 2, R=CH$_3$) has a very low fluorescence quantum yield of 13% with its dominant emission γ$_{max}$ 666 nm) in the near infra-red region of the spectrum where eyes are not very sensitive. The effect of contamination of this bis-condensed byproduct on the fluorescence efficiency of DCJT in 1,2-dichloroethane is shown in FIG. 4. The complication of this bis-condensation byproduct is altogether avoided in the synthesis these new red fluorescent materials making possible the isolation of much purer compounds directly without the need of lengthy purification procedures. Furthermore, it is also evident from Table 1 that these new materials all exhibit high luminescence efficiency comparable to that of DCJT. Particularly preferred are the t-butyl substituted dyes of DCJTB and DCMB. For substituted phenyl derivative, it is essential to have ortho-substituent such as mesityl group in DCJTM and DCMM so that the phenyl group is twisted out of conjugation with the dye chromophore, thus, preventing the fluorescence spectrum from shifting too far to the red.

Scheme 1
Synthesis of New Red Organic Electroluminescent Materials

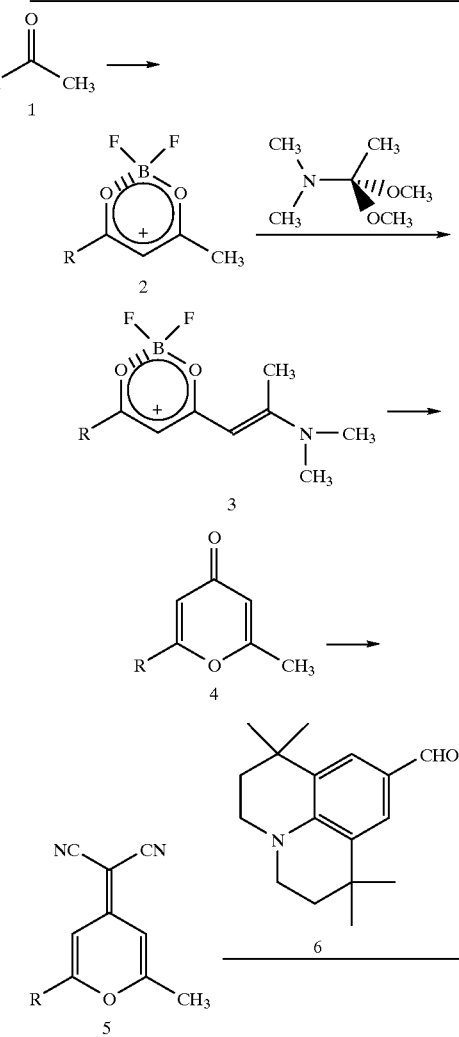

-continued

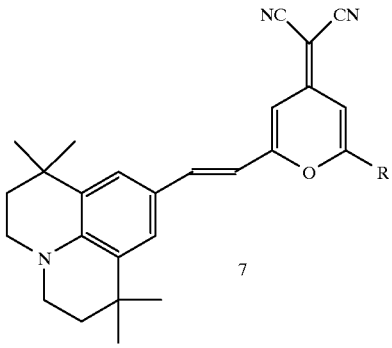

Preferred materials for use in forming the electron transporting layer of the organic EL devices of this invention are metal chelated oxinoid compounds, including chelates of oxine itself (also commonly referred to as 8-quinolinol or 8-hydroxyquinoline). Such compounds exhibit both high levels of performance and are readily fabricated in the form of thin films. Exemplary of contemplated oxinoid compounds are those satisfying the following structural formula:

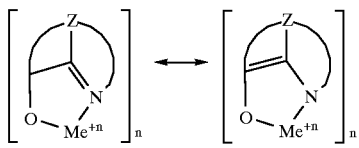

wherein

Me represents a metal;

n is an integer of from 1 to 3; and

Z independently in each occurrence represents the atoms completing a nucleus having at least two fused aromatic rings.

From the foregoing it is apparent that the metal can be monovalent, divalent, or trivalent metal. The metal can, for example, be an alkali metal, such as lithium, sodium, or potassium; an alkaline earth metal, such as magnesium or calcium; or an earth metal, such as boron or aluminum. Generally any monovalent, divalent, or trivalent metal known to be a useful chelating metal can be employed.

Z completes a heterocyclic nucleus containing at least two fused aromatic rings, at least one of which is an azole or azine ring. Additional rings, including both aliphatic and aromatic rings, can be fused with the two required rings, if required. To avoid adding molecular bulk without improving on function the number of ring atoms is preferably maintained at 18 or less.

Illustrative of useful chelated oxinoid compounds are the following:

Aluminum trisoxine [a.k.a, tris(8-quinolinol)aluminum]

Magnesium bisoxine [a.k.a. bis(8-quinolinol)magnesium]

Indium trisoxine [a.k.a., tris(8-quinolinol)indium]

Lithium oxine (a.k.a., 8-quinolinol lithium)

The preferred materials for the multi-layers of the organic EL medium are each capable of film-forming—that is, capable of being fabricated as a continuous layer having a thickness of less than 5000 Å. A preferred method for forming the organic EL medium is by vacuum vapor deposition. Extremely thin defect-free continuous layers can be formed by this method. Specifically, the individual layer thickness as low as about 50 Å can be constructed while still realizing satisfactory EL device performance. It is generally preferred that the overall thickness of the organic EL medium be at least about 1000 Å.

Other methods for forming thin films in EL devices of this invention include spin-coating from a solution containing the EL material. A combination of spin-coating method and vacuum vapor deposition method is also useful for the fabrication of multi-layer EL devices.

The anode and cathode of the organic EL device can each take any convenient conventional form. Where it is intended to transmit light from the organic EL device through the anode, this can be conveniently achieved by coating a thin conductive layer onto a light transparent substrate—e.g., a transparent or substantially transparent glass plate or plastic film. In one form the organic EL devices of this invention can follow the historical practice of including a light transparent anode formed of tin oxide or indium tin oxide coated on a glass plate, as disclosed by Gurnee et al U.S. Pat. No. 3,172,862, Gurnee U.S. Pat. No. 3,173,050, Dresner "Double Injection Electroluminescence in Anthracene", RCA Review, Volume 30, pages 322–334, 1969; and Dresner U.S. Pat. No. 3,710,167 cited above.

The organic EL devices of this invention can employ a cathode constructed of any metal, including any high or low work function metal, heretofore taught to be useful for this purpose. Unexpected fabrication, performance, and stability advantages have been realized by forming the cathode of a combination of a low work function metal and at least one other metal. For further disclosure, see U.S. Pat. No. 4,885,211 by Tang and Van Slyke, the disclosure of which is incorporated by reference herein.

EXAMPLES

According to the synthetic sequences outlined in Scheme 1, the invention and its advantages are further illustrated by the specific examples as follows:

Example 1—Synthesis of 2 (R=t-Bu)

To a solution of pinacolone (1, R=t-Bu) (100 g, 1 mol) in 204 g (2 mol) of acetic anhydride cooled with ice/water, was added dropwise 130 g of boron trifluoride etherate in about an hour. The reaction mixture was stirred overnight then rotary evaporated at 90° C. Upon cooling, the residue precipitated a solid which was filtered and washed with cold heptane to give 40 g of 2 (R=t-Bu) as a light yellow solid.

Example 2—Synthesis of 3 (R=t-Bu)

To a warmed (60° C.) solution of 80 g (0.42 mol) of 2 (R=t-Bu) and 4 mL of 2,6-lutidine in 70 g of dimethylacetamide was added dropwise 83 g (0.62 mol) of N,N-dimethylacetamide dimethyl acetal. The mixture was further heated at 85° C. for 2 h under nitrogen then cooled to filter the product that was precipitated giving 40 g of 3 (R=t-Bu) as a yellow solid.

Example 3—Synthesis of 4 (R=t-Bu)

A solution of 49 g (0.189 mol) of 3 (R=t-Bu), 87 mL of 70% perchloric acid, 87 mL of water in 870 mL of ethanol was refluxed for 2 h. Excess ethanol was stripped off. The residue was dissolved in water, made alkaline with ammonium hydroxide, extracted with ether. The organic phase was separated, rotary evaporated. The oily residue was added heptane, chilled in a dry ice/acetone bath to yield 38 g of crystalline product 4 (R=t-Bu) as a colorless solid.

Example 4—Synthesis of 5 (R=t-Bu)

A solution of 25 g (0.15 mol) of 4 (R=t-Bu), 12 g (0.2 mol) of malonitrile in 63 mL of acetic anhydride was heated at 120° C. until the reaction was complete by monitoring with TLC. The mixture was stripped under vacuum and the residue was chromatographed with a gradient of solvent mixture of heptane/methylene chloride over silica gel to give 25 g of crude product which was recrystallized to give 22 g of pure 5 (R=t-Bu).

Example 5—Synthesis of DCJTB (7,R=t-Bu)

A solution of 2.6 g (0.012 mol) of 5 (R=t-Bu), 3.12 g (0.012 mol) of 9-formyl-1,1,7,7-tetramethyljulolidine (6) and 0.35 mL of piperidine in 30 mL of acetonitrile was refluxed under nitrogen for 16 h. On cooling, the precipitated dye was filtered and washed with acetonitrile to give 2.4 g (yield=44%) of DCJTB (7, R=t-Bu). Mass spectrum: m/e 453 ($M^+$ for $C_{30}H_{35}N_3O$). HPLC using a Hewlett-Packard 1090 liquid chromatograph system equipped with a Superco Kodak HPLC column (Dupont RX LC-8, 15 cm) and a UV detector set at 440 nm, eluted with a gradient of solvents from 0.05 M $NH_4OAc$ (pH=4.65) in deionized water to acetonitrile confirmed the dye is 99.3% pure.

Example 6—Alternative Synthesis of DCJTB (7, R=t-Bu)

A solution of 224 mg (1.046 mmol) of 5 (R=t-Bu), 269 mg (1.046 mol) of 9-formyl-1,1,7,7-tetramethyljulolidine (6) and 4 drops each of piperidine and HOAc in 15 mL of toluene was azeotropically refluxed under nitrogen for 20 h. On cooling, the precipitated dye was filtered and washed with cold toluene to give 376 mg (yield=79%) of DCJBT (7, R=t-Bu). HPLC using a Hewlett-Packard 1090 liquid chromatograph system equipped with a Superco Kodak HPLC column (Dupont RX LC-8, 15 cm) and a UV detector set at 440 nm, eluted with a gradient of solvents from 0.05 M $NH_4OAc$ (pH=4.65) in deionized water to acetonitrile confirmed the dye is 99.3% pure.

The following examples exemplify the inevitable contamination of the bis-condensed dimer in DCJT synthesis as analyzed by HPLC:

Example 7—Synthesis of DCJT (7,R=$CH_3$)

A solution of 300 mg (1.74 mmol) of 5 (R=$CH_3$), 448 mg (1.74 mmol) of 9-formyl-1,1,7,7-tetramethyljulolidine (6) and 2 drops of piperidine in 10 mL of acetonitrile was refluxed under nitrogen for 20 h. On cooling, the precipitated dye was filtered and washed with acetonitrile to give 370 mg (yield=52%) of DCJT (7, R=$CH_3$). HPLC analysis using a Hewlett-Packard 1090 liquid chromatograph system equipped with a Superco Kodak HPLC column (Dupont RX LC-8, 15 cm) and a UV detector set at 440 nm eluted with a gradient of solvents from 0.05 M $NH_4OAc$ (pH=4.65) in deionized water to acetonitrile showed the dye is 94% pure contaminated with 5.5% of the bis-condensed byproduct (structure 2, R=$CH_3$). The contaminant was characterized by mass spectrum with m/e 650 ($M^+$) which corresponds to $C_{44}H_{50}N_4O$.

Example 8—Alternative Synthesis of DCJT (7, R=$CH_3$)

A solution of 259 mg (1.51 mmol) of 5 (R=$CH_3$), 387 mg (1.51 mmol) of 9-formyl-1,1,7,7-tetramethyljulolidine (6) and 4 drops each of piperidine/HOAc in 15 mL of toluene was azeotropically refluxed under nitrogen for 18 h. On cooling, the precipitated dye was filtered and washed with toluene to give 560 mg (yield=90%) of crude DCJT (7, R=$CH_3$). HPLC analysis was carried out by using a Hewlett-Packard 1090 liquid chromatograph system equipped with a Superco Kodak HPLC column (Dupont RX LC-8, 15 cm) and a UV detector set at 440 nm. The isolated product was dissolved in acetonitrile and eluted with a gradient of solvents from 0.05 M $NH_4OAc$ (pH=4.65) in deionized water to acetonitrile which showed the dye is only 80% pure contaminated with 19% of the bis-condensed byproduct (structure 2, R=$CH_3$). The contaminant was characterized by mass spectrum with m/e 650 ($M^+$) which corresponds to $C_{44}H_{50}N_4O$.

Example 9—EL Device Fabrication and Performance

An EL device satisfying the requirements of the invention was constructed in the following manner. For comparison, this example illustrates an organic EL device where the EL medium contains a red fluorescent DCJT (prior art) doped luminescent layer. The organic EL medium has four organic layers, namely, a hole-injection layer, a hole transport layer, a doped luminescent layer, and an electron-transport layer.

a) An indium-tin-oxide (ITO) coated glass substrate was sequentially ultrasonicated in a commercial detergent, rinsed in deionized water, degreased in toluene vapor and exposed to ultraviolet light and ozone for a few minutes.

b) A hole injection layer of copper phthalocyanine (150 Å) was then deposited on top of the ITO coated substrate by evaporation from a tantalum boat.

c) Onto the copper phthalocyanine layer was deposited a hole transport layer of N,N'-bis-(1-naphthyl)-N,N'-diphenylbenzidine (600 Å), also by evaporation from a tantalum boat.

d) A luminescent layer of Alq (375 Å) mixed with 0.9% (v/v) of the red fluorescent dopant—DCJT (R=CH3) was then codeposited onto the hole-transport layer.

e) A electron-transport layer of Alq (375 Å) was then deposited onto the luminescent layer.

f) On top of the Alq layer was deposited a cathode layer (2000 Å) formed of a 10:1 atomic ratio of Mg and Ag.

The above sequence completed the deposition of the EL device. The device was then hermetically packaged in a dry glove box for protection against ambient environment.

The light output from this EL device was 389 cd/$m^2$ when it was driven by a current source of 20 mA/$cm^2$ and a bias voltage of 12.65 volts. Its radiance is 1.66 W/Sr/$m^2$ and EL efficiency is 0.48 lm/W with a yield of 1.94 cd/A. Peak emission wavelength is 616 nm with a half-bandwidth of 84 nm. The EL color is red with 1931 CIE color coordinates of x=0.619 and y=0.376. This EL spectrum indicates that EL emission originates from the doped luminescent layer.

Example 10

This example illustrates the advantage of fabricating an organic EL device where the EL medium contains the red fluorescent DCJTB doped luminescent layer. The organic EL medium has four organic layers, namely, a hole-injection layer, a hole transport layer, a doped luminescent layer, and an electron-transport layer.

a) An indium-tin-oxide (ITO) coated glass substrate was sequentially ultrasonicated in a commercial detergent, rinsed in deionized water, degreased in toluene vapor and exposed to ultraviolet light and ozone for a few minutes.

b) A hole injection layer of copper phthalocyanine (150 Å) was then deposited on top of the ITO coated substrate by evaporation from a tantalum boat.

c) Onto the copper phthalocyanine layer was deposited a hole transport layer of N,N'-bis-(1-naphthyl)-N,N'-diphenylbenzidine (600 Å), also by evaporation from a tantalum boat.

d) A layer of doped Alq (375 Å) was then deposited onto the hole-transport layer. The doped layer contains 0.9% (v/v) of the red fluorescent DCJTB which was co-deposited with the Alq to form a uniform doped luminescent layer.

e) A electron-transport layer of Alq (300 Å) was then deposited onto the luminescent layer.

f) On top of the Alq layer was deposited a cathode layer (2000 Å) formed of a 10:1 atomic ratio of Mg and Ag.

The above sequence completed the deposition of the EL device. The device was then hermetically packaged in a dry glove box for protection against ambient environment.

Figure 5:
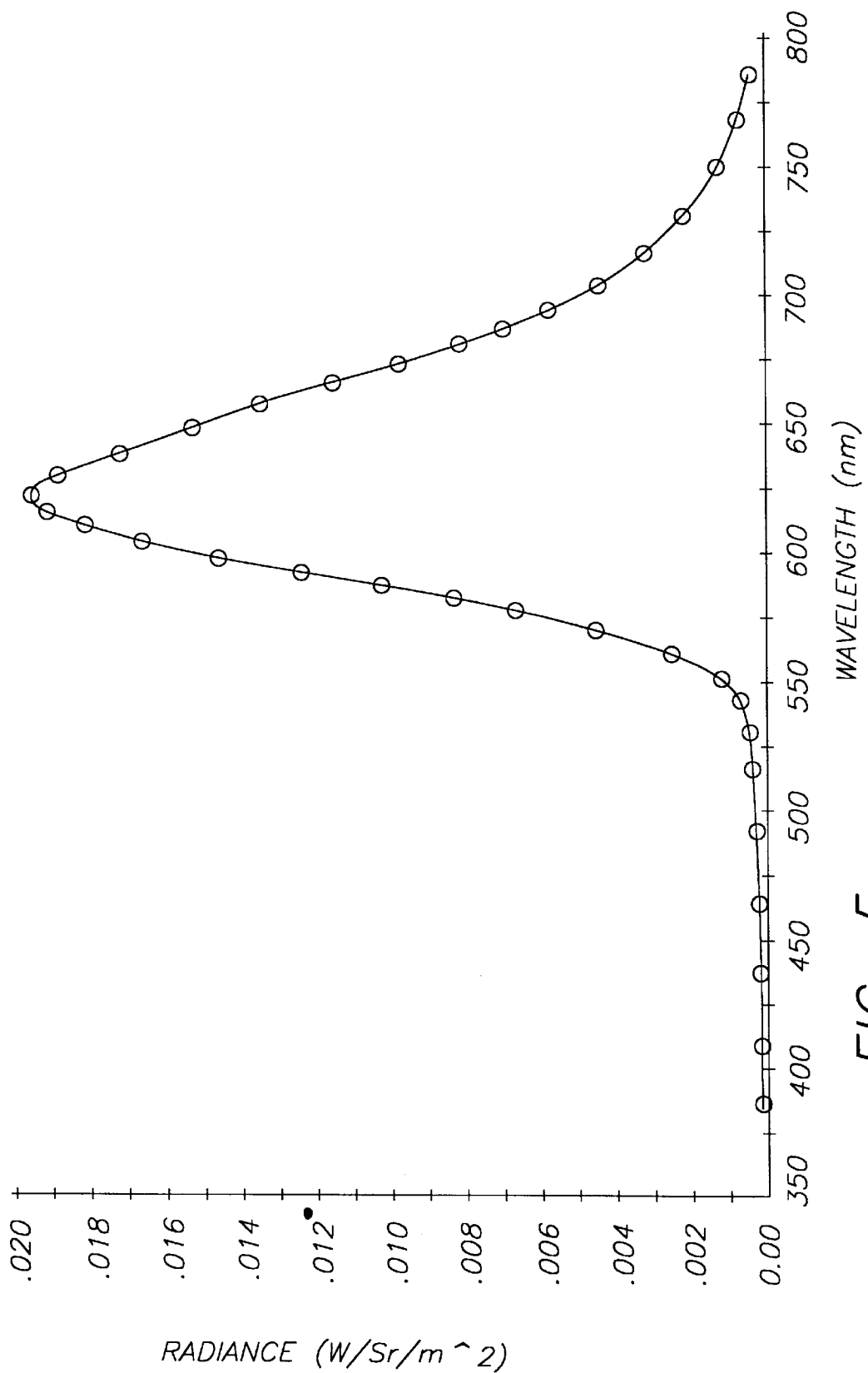
FIG. 5 shows the plot of the spectral characteristics of an EL device which uses the compound DCJTB as red dopant in accordance with the present invention.

The light output from this EL device was 400 cd/m$^2$ when it was driven by a current source of 20 mA/cm$^2$ and a bias voltage of 13.14 volts. The EL color is red with 1931 CIE color coordinates of x=0.627 and Y=0.369. Its radiance is 1.83 W/Sr/m$^2$ and EL efficiency is 0.48 lm/W with a yield of 2.0 cd/A. The EL spectrum shown in FIG. 5 has a peak emission at 620 nm with a half bandwidth of 88 nm. This EL spectrum indicates that EL emission originates from the red fluorescent dye doped Alq layer and is predominantly characteristic of the red dopant DCJTB. The red color of electroluminescence of this device appears deeper and slightly more saturated and its efficiency is also somewhat higher than that of DCJT doped device driven under similar conditions described in the previous example.

The invention has been described in detail with particular reference to certain preferred embodiments thereof, but it will be understood that variations and modifications can be effected within the spirit and scope of the invention.

| PARTS LIST | |
|---|---|
| 100 | EL Device |
| 102 | Substrate |
| 104 | Anode |
| 106 | Cathode |
| 108 | Organic EL medium |
| 110 | Hole-transport layer |
| 112 | Electron-transport layer |
| 114 | External power source |
| 116 | Conductor |
| 118 | Conductor |
| 120 | Holes |
| 122 | Electrons |
| 200 | EL device |
| 202 | Substrate |
| 204 | Anode |
| 206 | Cathode |
| 208 | Organic EL medium |
| 210 | Hole-transport layer |
| 212 | Luminescent layer |
| 214 | Electron-transport layer |
| 300 | EL device |
| 302 | Substrate |
| 304 | Anode |
| 306 | Cathode |
| 308 | Organic EL medium |
| 310 | Hole-injection layer |
| 312 | Hole-transport layer |
| 314 | Luminescent layer |
| 316 | Electron-transport layer |
| 318 | Electron-injection layer |

What is claimed is:

1. A compound of the formula:

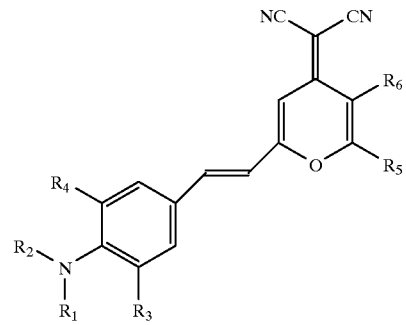

wherein:

$R_1$, and $R_2$ are individually alkyl of from 1 to 20 carbon atoms, aryl, or heteroaryl; and $R_3$, and $R_4$ are individually alkyl of from 1 to 10 carbon atoms, or a $R_3R_4$ ring connected with $R_1$, $R_2$ respectively to form a 5 or 6 member substituted or unsubstituted ring; and $R_5$ is t-butyl; sterically hindered aryl or heteroaryl; perhaloalkyl of 1–10 carbon atoms and $R_6$ is hydrogen or $R_5$ and $R_6$ together form a 5 or 6 member carbocylic ring.

2. The compound of claim 1 wherein $R_1$ and $R_2$ are methyl, ethyl, propyl, n-butyl, aryl or heteroaryl, $R_3$ and $R_4$ are methyl, ethyl, propyl, n-butyl, i-propyl, t-butyl, sec-butyl, or t-amyl, or $R_3$ and $R_4$ are arranged respectively with $R_1$ and $R_2$ as follows $R_1,R_3=R_2,R_4=\{CH_2CH_2\}$, $\{CH_2CH_2CH_2\}$, or $CH_2CH_2C(CH_3)_2$ and $R_5$ is t-butyl, sterically hindered 1-naphthyl, 9-anthracenyl, pyrenyl, perylenyl, mesityl, 2,4-dimethylphenyl, 2-methylphenyl, trifluoromethyl, pentafluoroethyl, perfluoroalkyl or $R_5,R_6$ together=$(CH_2CH_2CH_2-)$ or $(CH_2CH_2CH_2CH_2-)$.

3. A compound of the formula:

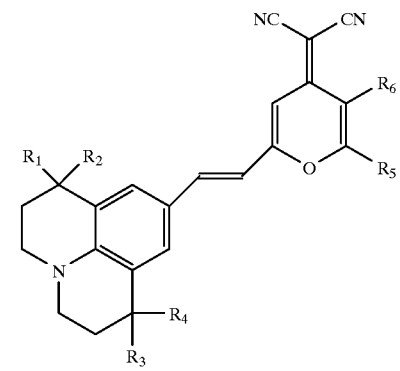

wherein:

$R_1$, $R_2$, $R_3$, and $R_4$ are individually alkyl of from 1 to 10 carbon atoms; halogen;

$R_5$ is t-butyl; sterically hindered aryl or heteroaryl; perhaloalkyl of 1–10 carbon atoms and $R_6$ is hydrogen or $R^5$ and $R^6$ together form a 5 of 6 member carbocyclic ring.

4. The compound according to claim 3 wherein $R_1$, $R_2$, $R_3$ and $R_4$ are methyl, ethyl, propyl, n-butyl, i-propyl; aryl or heteroaryl, heterocyclic systems; chloro, fluoro and wherein $R_5$ is t-butyl, or sterically hindered 1-naphthyl, 9-anthracenyl, pyrenyl, perylenyl, or mesityl, 2,4-dimethylphenyl, 2-methylphenyl trifluoromethyl, pentafluoroethyl, perfluoroalkyl or $R_5$, $R_6$ together=(—CH$_2$CH$_2$CH$_2$—) and (—CH$_2$CH$_2$CH$_2$CH$_2$—).

5. The compound of claim 1, wherein $R_5$ is t-butyl.

6. The compound of claim 1, wherein $R_5$ is sterically hindered aryl or heteroaryl.

7. The compound of claim 1, wherein $R_5$ is mesityl.

8. A compound according to claim 5, which is 4-dicyanomethylene)-2-t-butyl-6-(1,1,7,7-tetramethyljulolidyl-9-enyl)-4H-pyran.

9. A red fluorescent material comprising a compound according to claim 1.

10. A red fluorescent material comprising a compound according to claim 3.

* * * * *